United States Patent [19]
Kirchner et al.

[11] Patent Number: 5,902,737
[45] Date of Patent: May 11, 1999

[54] PROCESS FOR THE PREPARATION OF DISODIUM BENZYLOXYCARBONYL-L-ASPARTATE FROM FUMARIC ACID

[75] Inventors: Gerald Kirchner, Wesel, Germany; Erik Salzbrenner, Walding; Christian Werenka, Ansfelden, both of Austria; Wilhelmus Boesten, Sittard, Netherlands

[73] Assignees: DSM Fine Chemicals Austria GmbH, Austria; Holland Sweetener Company V.o.V., Netherlands

[21] Appl. No.: 08/934,141

[22] Filed: Sep. 19, 1997

[30] Foreign Application Priority Data

Sep. 20, 1996 [AT] Austria ..................................... 1672/96
Feb. 19, 1997 [AT] Austria ..................................... 272/97

[51] Int. Cl.$^6$ .............................. C12P 13/20; C12P 13/04
[52] U.S. Cl. ....................... 435/106; 435/109; 426/548; 560/40; 560/41; 562/445; 562/450
[58] Field of Search ..................................... 435/106, 109; 560/40, 41; 426/548; 562/445, 450

[56] References Cited

U.S. PATENT DOCUMENTS

| | | |
|---|---|---|
| 3,198,712 | 8/1965 | Takahashi et al. . |
| 3,791,926 | 2/1974 | Chibata et al. .......................... 435/109 |
| 4,326,029 | 4/1982 | Yukawa et al. .......................... 435/109 |
| 4,574,091 | 3/1986 | Steensen et al. .......................... 426/548 |
| 4,656,136 | 4/1987 | Kisumi et al. .......................... 435/109 |
| 4,680,403 | 7/1987 | Hisamitsu et al. ....................... 546/247 |

FOREIGN PATENT DOCUMENTS

| | | |
|---|---|---|
| 0 110 422 | 6/1984 | European Pat. Off. . |
| 0 127 940 | 12/1984 | European Pat. Off. . |

*Primary Examiner*—Herbert J. Lilling
*Attorney, Agent, or Firm*—Wenderoth, Lind & Ponack, L.L.P.

[57] ABSTRACT

A process for the preparation of disodium Z-L-aspartate from fumaric acid, in which
a) fumaric acid is reacted with ammonia in an inert diluent in the presence of aspartase or aspartase-producing microorganisms to give ammonium L-aspartate then
b) the ammonium L-aspartate-containing solution is treated with sodium hydroxide, forming, depending on the amount of sodium hydroxide used, the mono- or disodium L-aspartate or a mixture thereof, and
c) the eliminated ammonia is returned to a fumaric acid suspension, which is used as starting solution for further enzymatic reactions, and then
d) the residual mono and/or disodium L-aspartate-containing solution is reacted with benzyloxycarbonyl chloride at a pH of between 9 and 14, with the simultaneous addition of sodium hydroxide, to form disodium Z-L-aspartate.

10 Claims, No Drawings

PROCESS FOR THE PREPARATION OF DISODIUM BENZYLOXYCARBONYL-L-ASPARTATE FROM FUMARIC ACID

L-aspartic acid is an essential starting material in the synthesis of the dipeptide aspartame, an artificial sweetener having around 200 times the sweetening power of sucrose.

A large number of chemical and enzymatic processes have already been described for the synthesis of aspartame, in which, in particular L-aspartic acid and phenylalanine methyl ester are coupled together in a variety of different ways, for example with or without enzymatic catalysis. For example, solid aspartic acid is converted into the disodium salt, and then reacted with benzyloxycarbonyl chloride (Z-Cl) in aqueous solution to give disodium Z-L-aspartate. Aspartic acid is prepared, as described for example in EP-A-0 127 940, from maleic acid, which is isomerized to give fumaric acid, by an enzymatic route via ammonium L-aspartate and subsequent crystallization in the presence of an acid. Equimolar quantities of ammonium salts are produced in the mother liquor and have to be suitably disposed of. Also, a large number of steps is required to obtain disodium Z-L-aspartate where Z is benzyloxycarbonyl.

The object of the present invention was therefore to find a process which does not produce the ammonium ion-containing waste water and in which the number of steps to give the disodium Z-L-aspartate is reduced.

Surprisingly, this object has been achieved by a process in which, starting from fumaric acid, ammonium L-aspartate is converted directly into the disodium salt of L-aspartic acid with simultaneous quantitative recycling of the ammonia.

Accordingly, the present invention relates to a process for the preparation of disodium Z-L-aspartate from fumaric acid, wherein a) fumaric acid is reacted with ammonia in an inert diluent in the presence of aspartase or aspartase-producing microorganisms to give ammonium L-aspartate, then b) the ammonium L-aspartate-containing solution is treated with sodium hydroxide, forming, depending on the amount of sodium hydroxide used, the mono- or disodium L-aspartate or a mixture thereof, and c) the eliminated ammonia is returned to a fumaric acid suspension, which is used as starting solution for further enzymatic reactions, and then d) the residual mono- and/or disodium L-aspartate-containing solution is reacted with benzyloxycarbonyl chloride at a pH of between 9 and 14, with the simultaneous addition of sodium hydroxide, to form disodium Z-L-aspartate.

In the first step a) of the process according to the invention, fumaric acid is converted into ammonium L-aspartate in an enzymatic reaction. The starting material for the process according to the invention, fumaric acid, can for example be prepared by isomerization of maleic acid.

For the enzymatic reaction, fumaric acid is stirred into an inert diluent until the solubility limit is reached, so that a suspension is obtained. Suitable inert diluents are water or water/ethanol or water/acetone mixtures and the like.

Preference is given to water. Ammonia, which is liquefied or in the form of a 10 to 35% strength by weight solution, is then introduced into the fumaric acid suspension at room temperature, as a result of which the temperature rises to 60° C. and the pH adjusts to between 8 and 9.

An aqueous 20 to 30% strength by weight ammonia solution is preferably used. The enzyme aspartase or an aspartase-producing microorganism is then stirred into the resultant system, preferably a solution, at 20 to 60° C., preferably 30 to 50° C. When adding this enzyme or aspartase-producing microorganism, it is advantageous if the addition of ammonia gives a solution, since a suspension requires more enzyme as a result of enzyme adsorption and associated loss in activity. 30 to 50 IU (enzyme activity) per mole of fumaric acid are required for an almost quantitative conversion after 24 to 30 hours.

Aspartase-producing microorganisms are, for example, *Pseudomonas fluorescens, Proteus vulgaris, Pseudomonas aeruginosa, Serratia marcescens, Bacterium succinium, Bacillus subtilis, Aerobacter aerogenes,* Hicrococcus sp. and *Escherichia coli* etc.

Other suitable aspartase-producing microorganisms are, for example, described in U.S. Pat. Nos. 3,791,926 and 3,198,712.

Purified or synthetic aspartase can also be used for the process according to the invention. The enzyme or the aspartase-producing microorganism can be used in liquid or in immobilized form, as described for example in EP 0 127 940.

When the reaction is complete (the end of the reaction can be determined for example by photometric means), the solution which contains the ammonium L-aspartate is preferably cooled to 20 to 30° C. and treated with sodium hydroxide in the 2nd step (b). The quantity of sodium hydroxide added depends on the desired sodium salt. Both the monosodium and the disodium salt and mixtures thereof are suitable for the further reaction. Sodium hydroxide can be used in solid form or as sodium hydroxide solution. Preference is given to sodium hydroxide solution. The reaction solution warms to approximately 40 to 60° C. The eliminated and escaping ammonia is introduced, for example in another reaction vessel using a submerged tube, into a fumaric acid suspension which, after the further addition of ammonia, can be reused as starting solution for the next enzymatic reaction (step c).

In order to remove the ammonia from the reaction solution, a temperature of between approximately 50 and 100° C. is used and most of the ammonia is expelled at a pressure of between atmospheric and 80 to 120 mbar.

After approximately 0.5 to 10 hours, if necessary, nitrogen is bubbled through the reaction solution under a vacuum of 200 to 300 mbar, and a temperature of 55 to 65° C. is maintained so that the residual ammonia is also removed.

The resultant mono- and/or disodium L-aspartate solution is then treated with Benzyloxycarbonyl chloride (Z-Cl) in the next stage d) at a temperature of 30 to 60° C., a pH of between 9 and 14, preferably between 11 and 12, being maintained by the simultaneous dropwise addition of sodium hydroxide solution Z-Cl can be added in an equimolar quantity or alternatively in a slight excess. After the Z-Cl has been added, the reaction mixture is left to stand for a further 0.5 to 4 hours and then cooled to room temperature, which results in phase separation.

The aqueous phase is then washed, for example using methyl tert-butyl ether, diisobutyl ether, toluene or other water-immiscible solvents.

The organic phase is discarded and Z-L-aspartic acid is obtained as the disodium salt in aqueous solution. To remove any residual organic solvents which may be present in the aqueous phase, a vacuum is applied at room temperature.

The process according to the invention produces disodium Z-L-aspartate as a clear, slightly yellowish solution which, if required, can be further converted into aspartame by coupling with phenylalanine. In the process according to the invention, no ammonium ion-containing waste water is produced, and ammonia is recycled in quantitative amounts for further enzymatic reactions of fumaric acid.

Furthermore, in the process according to the invention, it is not necessary to isolate L-aspartic acid or one of the intermediates.

EXAMPLE 1 a) Enzymatic Reaction 2070 ml of drinking water were placed in a 5 l double-walled vessel and 973 g of fumaric acid (8.38 mol) were stirred into it. 1450 ml of 25% strength by weight ammonia solution (1314 g) were then introduced into the fumaric acid suspension over the course of 30 minutes. A reaction temperature of 45–50° C. and a pH of 8.5 was reached. 1.4 ml of aspartase solution (245 IU/ml) were introduced into the clear solution at 45° C. and with gentle stirring. The stirrer was then switched off and the reaction solution maintained at 45° C. The course of the reaction was monitored by photometric means. Virtually quantitative conversion (>99%) was achieved after 25.5 hours.

b) and c) Expulsion of Ammonia

After the solution obtained in a) had been cooled to 25° C., 1330 g of 50% strength by weight sodium hydroxide solution were introduced over the course of 15 minutes. The solution warmed to 50° C. and a pH of 11.5 was measured. The escaping ammonia was introduced into a fumaric acid suspension using a submerged tube (fumaric acid/ammonia wash solution). The amounts of water and fumaric acid were the same as given in a). By heating to 57° C. and applying a vacuum of 100 mbar, most of the ammonia was expelled. After 6 hours, nitrogen was bubbled through the reaction solution (20 l/h). The temperature was raised to 60° C. and a vacuum of 240 mbar was applied (duration 4.5 hours). The total amount of distillate was approximately 1100 g. Residual ammonia content <100 ppm.

Disodium L-aspartate solution containing 23.5% by weight of L-aspartic acid was obtained. No racemization was observed.

The content of fumaric acid was <0.1% by weight; malic acid and asparagine were not detected.

d) Preparation of Disodium Z-(L)-aspartate 80 ml of a disodium L-aspartate solution with 18.1% by weight of L-aspartic acid (0.11 mol) prepared as in Example 1a–c) were heated to 45° C. 20.5 g of benzyloxycarbonyl chloride (Z-Cl) (content: 92.5 according to GC) (0.11 mol) were added dropwise with stirring over the course of 1 hour. At the same time, the pH was maintained at between 10.9 and 13.8 by the dropwise addition of 50% strength by weight sodium hydroxide solution. In total, 7.8 g of 50% strength by weight sodium hydroxide solution were added. Following the dropwise addition, the reaction solution was maintained at 45–47° C. for 2.5 hours. The pH was a constant 12.1. After cooling to 25° C., the aqueous solution was treated twice with 92 ml of methyl tert-butyl ether. The organic phase was discarded; solvent residues were removed from the aqueous phase in a rotary evaporator at 20° C. and 20 mbar in 30 minutes.

101 g of a slightly yellowish, clear solution were obtained whose content of disodium Z-(L)-aspartate was 30.8% by weight (calculated as L-aspartic acid).

EXAMPLE 2

Preparation of Monosodium L-aspartate Solution

As in Example 1 b) and c), 588 g of 20% strength by weight sodium hydroxide solution were introduced, over the course of 15 minutes, into 1300 ml of a solution obtained as described in 1a) which had been cooled to 25° C. The solution warmed to 50° C. The escaping ammonia was introduced into a fumaric acid suspension using a submerged tube (fumaric acid/aemonia wash solution). The quantities of water and fumaric acid were the same as those given in a). All the ammonia was expelled at atmospheric pressure and the reaction solution was evaporated to 1200 ml. Residual ammonia content <300 ppm.

A monosodium L-aspartate solution containing 25.9% by weight of L-aspartic acid was obtained. No racemization was observed.

The content of fumaric acid was <0.1% by weight; malic acid and asparagine were not detected.

The solution was further worked up as in Example 1d to give disodium Z-(L)-aspartate.

EXAMPLE 3

Preparation of Disodium Z-(L)-aspartate with an Excess of Z-Cl 64.2 ml of a disodium L-aspartate solution with 18.1% by weight of L-aspartic acid were heated to 45° C. (0.09 mol), prepared as in Example 1 a–c. 17.7 g of benzyloxycarbonyl chloride (Z-Cl, content: 92.5 according to GC) (0.10 mol) were added dropwise with stirring over the course of 1 hour. At the same time, the pH was maintained between 9.4 and 11.8 by the dropwise addition of 50% strength by weight sodium hydroxide solution. In total, 8.8 g of 50% strength by weight sodium hydroxide solution were added. Following the dropwise addition, the reaction solution was maintained at 45° C. for 2.5 hours. The pH was a constant 11.3. After cooling to 25° C., the aqueous solution was treated twice with 46 ml of methyl tert-butyl ether. The organic phase was discarded; solvent residues were removed from the aqueous phase in a rotary evaporator at 20° C. and 20 mbar in 30 minutes.

84.2 g of a slightly yellowish, clear solution were obtained whose content of disodium Z-(L)-aspartate was 31.4% by weight (calculated as L-aspartic acid).

EXAMPLE 4

Enzymatic Reaction of Fumaric Acid/Ammonia Wash Solution

After the experiment was complete, the fumaric acid/ammonia wash solution obtained in Example 1 a–c was adjusted to pH 8.5 using 514 g of 25% by weight ammonia and worked up further as in Example 1 a–c to give disodium L-aspartate solution.

The results are given in Table 1.

TABLE 1

| Experiment | | 1. | 2. | 3. | 4. | 5. |
|---|---|---|---|---|---|---|
| Water | (ml) | 2070 | 2000 | 2423 | 2450 | 2100 |
| Fumaric acid | (g) | 973 | 973 | 973 | 973 | 973 |
| Ammonia | (g) | 1314 | 514 | 752 | 570 | 643 |
| pH | at 45° C. | 8.5 | 8.18 | 8.48 | 8.48 | 8.4 |
| Enzyme solution | (ml) | 1.4 | 1.4 | 2.1 | 2.1 | 1.4 |

TABLE 1-continued

| Experiment | | 1. | 2. | 3. | 4. | 5. |
|---|---|---|---|---|---|---|
| Duration | (h) | 25.5 | 24 | 16 | 15 | 28 |
| Reaction | (%) | >99 | >99 | >99 | 98.6 | >99 |
| 50% NaOH | (g) | 1330 | 1229 | 1316 | 1333 | 1312 |
| pH | | 11.5 | 11.9 | 11.6 | 11.9 | 11.8 |
| T max | (° C.) | 57 | 51 | 53 | 66 | 59 |
| Vacuum | (mbar) | 100 | 174 | 120 | 200 | 170 |
| Duration | (h) | 6 | 1 | 2.5 | 3.5 | 2.75 |
| $N_2$ purge | 1/h | 20 | 35 | 30 | 30 | 30 |
| Temp. | (° C.) | 61 | 60 | 59 | 70 | 63 |
| Vacuum | (mbar) | 240 | 300 | 250 | 250 | 210 |
| Duration | (h) | 4.5 | 5 | 3 | 1 | 1 |
| Content | (% L-asp) | 23.5 | 18.2 | 21.4 | 22.6 | 20.7 |

The resultant disodium L-aspartate solutions were converted into disodium Z-L-aspartate as in Example 1d and Example 3.

We claim:

1. A process for the preparation of disodium benzyloxycarbonyl-L-aspartate from fumaric acid, wherein
   a) fumaric acid is reacted with ammonia in an inert diluent in the presence of aspartase or aspartase-producing microorganisms to give ammonium L-aspartate, then
   b) the ammonium L-aspartate-containing solution is treated with sodium hydroxide, forming, depending on the amount of sodium hydroxide used, the mono- or disodium L-aspartate or a mixture thereof, and
   c) the eliminated ammonia is returned to a fumaric acid suspension, which is used as starting solution for further enzymatic reactions, and then
   d) the residual mono- and/or disodium L-aspartate-containing solution is reacted with benzyloxycarbonyl chloride at a pH between 9 and 14, with the simultaneous addition of sodium hydroxide, to form disodium benzyloxycarbonyl-L-asparate.

2. The process as claimed in claim 1, wherein the inert diluent used is water or water/ethanol or water/acetone mixtures.

3. The process as claimed in claim 1, wherein the ammonia used is liquefied or in the form of an aqueous 10 to 35% strength by weight solution.

4. The process as claimed in claim 1, wherein fumaric acid is reacted in the presence of 30 to 50 IU (enzyme activity) per mole of fumaric acid.

5. The process as claimed in claim 1, wherein all the eliminated ammonia is removed from the reaction solution at a pressure of between atmospheric and 80 to 120 mbar at 50 to 100° C. and, if necessary, with subsequent bubbling of nitrogen at 200 to 300 mbar and 55 to 65° C.

6. The process as claimed in claim 1, wherein the reaction of benzyloxycarbonyl chloride with the mono- and/or disodium L-aspartate-containing solution is carried out at pH of between 11 and 12.

7. The process as claimed in claim 1, wherein benzyloxycarbonyl chloride is added to the mono- and/or disodium L-aspartate-containing solution at 30 to 60° C.

8. The process as claimed in claim 1 wherein, subsequent to the reaction of mono- and/or disodium L-aspartate and benzyloxycarbonyl chloride, phase separation into an aqueous phase containing the disodium benzyloxycarbonyl-L-aspartate and an organic phase takes place and the aqueous phase is washed with a water-immiscible solvent.

9. The process as claimed in claim 8, wherein the water-immiscible solvent is methyl tert-butyl ether, diisopropyl ether or toluene.

10. The process as claimed in claim 8, wherein the aqueous phase which contains the disodium benzyloxycarbonyl-L-aspartate is used for further conversion into aspartame by coupling with phenylalanine.

* * * * *